United States Patent [19]

Yoshimoto et al.

[11] Patent Number: 4,954,438

[45] Date of Patent: Sep. 4, 1990

[54] PROCESS FOR PREPARING ANTIBIOTICS D788-7

[75] Inventors: Akihiro Yoshimoto, Fujisawa; Osamu Jodo, Yokohama; Yoshio Watanabe; Rokuro Okamoto, both of Fujisawa; Tomio Takeuchi, Tokyo, all of Japan

[73] Assignee: Sanraku Incorporated, Tokyo, Japan

[21] Appl. No.: 397,061

[22] Filed: Aug. 21, 1989

[30] Foreign Application Priority Data

Aug. 25, 1988 [JP] Japan ................................. 63-211623

[51] Int. Cl.⁵ .................. C12P 19/56; C07H 15/24
[52] U.S. Cl. .................................. 435/78; 204/157.64;
204/157.82; 424/116; 424/120; 424/122;
435/170; 435/173; 435/252.35; 435/886;
514/34; 536/6.4; 536/18.4; 552/201
[58] Field of Search ...................... 424/116, 120, 122;
514/34; 435/78, 170, 252.35, 886, 173; 536/6.4,
18.4; 552/201; 204/157.64, 157.82

[56] References Cited

U.S. PATENT DOCUMENTS 4,612,371 9/1986 Yoshimoto et al. ................. 536/6.4

FOREIGN PATENT DOCUMENTS 8300 1/1985 Japan .

*Primary Examiner*—Herbert J. Lilling
*Attorney, Agent, or Firm*—Jordan and Hamburg

[57] ABSTRACT

This invention relates to a process for preparing an antibiotic D788-7 wherein, after culturing carborubicin-producing bacteria, the obtained culture liquid is extracted in acidic conditions while stirring to be absorbed to synthetic resin, followed by desorption from the resin and elution with acetone and the resulting acetone solution containing carborubicin is converted into an antibiotic D788-7 by photo radiation, for obtaining D788-7 in the purified form from the reaction solution. The production yield for D788-7 is extremely high and its use as an antitumor agent can be made possible.

5 Claims, No Drawings

PROCESS FOR PREPARING ANTIBIOTICS D788-7

BACKGROUND OF THE INVENTION

1. Field of the Invention

This invention relates to a process for preparing an antibiotic D788-7 useful as an antitumor antibiotic from carborubicin of an anthracycline antibiotic by chemical process in high yield.

2. Description of the Prior Art

D788-7 of the anthracycline antibiotic is the substance to be extracted from the culture medium where a variant strain of Streptomyces sp. D788 is cultured. It is known as a substance with superior antitumor activity (Japanese Patent Kokai No. 61-33194).

The anthracycline antibiotic carborubicin is a known antibiotic, which may be obtained by culturing Streptomyces coeruleorubidus strain (Japanese Patent Kokai No. 60-8300).

The anthracycline antibiotic D788-7 has a strong antitumor activity against various experimental tumors and its development as an antitumor agent has been expected.

As for the preparation of the substance, a process by the culture of Streptomyces sp. D788 strain has already been invented by the inventors (Japanese Patent Kokai No. 61-33194). However, in this process, the yield is extremely low and thus a process for its preparation in high yield has been desired.

SUMMARY OF THE INVENTION

The object of this invention is to provide a process for preparing a useful antibiotic D788-7 in high yield.

The inventors have intensively studied about the biosynthetic pathway of the antibiotic D788-7 in the producing strain and have found that the substance was produced from carborubicin, a specific anthracycline antibiotic disclosed previously by the inventors (Japanese Patent Kokai No. 60-8300); it was produced via the connective enzymatic reactions where the decarboxylation of carborubicin proceeded simultaneously with the hydroxylation. However, the activity of the D788-7 - producing enzyme, which converts carborubicin biochemically into the antibiotic D788-7, is very weak and therefore a great amount of carborubicin is likely to be accumulated. Thus, it has been difficult to produce D788-7 in high yield.

Thus, after the intensive efforts, the inventors focused on a process for preparing D788-7 by chemical treatment of carborubicin and achieved the process for preparation of the useful antibiotic D788-7 by exposing the carborubicin solution to light, the resulting yield being quite high, i.e. 70% or more.

The invention comprises the process for preparing the antibiotic D788-7 by exposing carborubicin in acetone to light, and the process for obtaining D788-7 wherein, after carborubicin-producing strain are cultured, the resulting culture liquid is extracted in acidic conditions under the stirring condition and filtrated. The supernatant was adsorbed on a column of synthetic resin followed by desorption from the resin and elution with acetone, and then the obtained acetone solution containing carborubicin is exposed to light for conversion into the antibiotic D788-7, which was recovered by solvent extraction and purified by a column chromatography with synthetic resin.

Carborubicin for use in this invention is an anthracycline antibiotic expressed in formula (I).

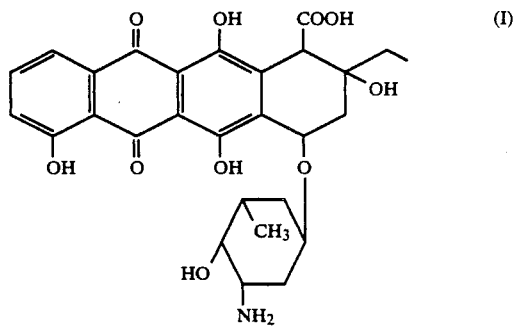

The substance is a known substance disclosed in Japanese Patent Laid-open No. 60-8300 and the process disclosed therein comprises;

A microbial strain belonging to the genus Actinomycetes, which produce daunomycin, carminomycin and their related compounds, for example *Streptomyces coeruleorubidus* 8899 (NRRL3046), Streptomyces coeruleorubidus ME130-A4 (FERM P-3540 and ATCC31276), *Streptomyces peucetius* (N.c.I.B9475), *Streptomyces griseus var. rubidofaciens* DS 32041, *Streptomyces bifurcus* DS23219 (NRR13539), *Streptosporangium sp-C-31751* (ATCC31129), *Streptosporangium sp. C-31751* (ATCC31129), *Actinomadura reseoviolacea var. biwakoensis* nov var. (FERM-P5155), or carborubicin-producing strain isolated therefrom by the known mutational treatment, was cultivated in a medium, the composition of which is suitable for producing carborubicin, and the culture broth was centrifuged on filtrated with the aid of filtering agents such as kieselguhr. The resulting supernatant, after concentration, was treated by a single or combined use of adsorbing carriers such as synthetic adsorbing resins, or chromatographed on a column of silica gel, anionic exchange resin or cationic exchange resin to obtain the purified carborubicin. The photochemical conversion reaction of the invention is preferably carried out in acetone solution, particularly at a concentration of 50-100%.

However, in order to prepare D788-7 consistently from the process for carborubicin production for convenience of industrial production, carborubicin is extracted from the cultured broth of carborubicin-producing strain in acidic conditions into the supernatant under continuous stirring and adsorbed to the synthetic adsorption resin followed by desorption from the resin and elution with 40-100% acetone, Then, the acetone solution of carborubicin eluted is used for the above conversion process.

The temperature for the above treatment is suggested to be around 5°-30° C., preferably around 20° C. and the period for photo-radiation depends on the intensity of light source and the concentration of carborubicin. Generally, the reaction completes within about 30-120 minutes.

The photochemical conversion reaction proceeds at pH 3-7, preferably at pH 5.0-5.4 and the buffers of this pH region may preferably be added in order to maintain this optimum pH. In this case, citrate buffer may be used advantageously.

Furthermore, when various additives were examined to promote this reaction, it was found that the addition of iodine remarkably promoted the reaction to improve the yield of D788-7. The amount of added iodine is 10 μg/ml–5 mg/ml, preferably around 100 μg/ml–2 mg/ml and more specifically the ratio between the concentration of iodine and that of carborubicin is about 1:1. When the photochemical conversion reaction proceeds by the addition of iodine in this manner, the conversion rate of carborubicin into D788-7 reaches 70%.

In order to isolate and purify D788-7 from the conversion reaction solution, the solution is adjusted to pH 2 with mineral acid, for example, sulfuric acid to remove the organic acid by evaporation. After the concentrate is adjusted to pH 7–9 with sodium hydroxide, D788-7 is extracted with an organic solvent such as chloroform, butanol and ethylacetate or after the concentrate is diluted with an equal or more than equal volume of water and adjusted to pH 7–9 with sodium hydroxide, D788-7 is extracted with chloroform. The extract thus obtained is concentrated for dryness to give crude D788-7. This preparation is treated with a single or combined use of column chromatograph of adsorbing carriers such as synthetic adsorbing resins, silica gel, anionic exchange resin or cationic exchange resin, to obtain the purified D788-7.

Moreover, crude powder thereof can be crystallized in chloroform-methanol or acetone in the form of hydrochloride to give the purified product.

The substance obtained in this manner shows the analytical values identical to those of authentic sample in the following instrumental analyses such as $^1$H—NMR and $^{13}$C—NMR spectra, FD mass spectrum, UV and visible absorption spectra, infrared absorption spectrum, etc., (see J. Antibiotics, vol. 39, pp. 902–909) and after acid hydrolysis of the substance, β-rodomycinone as an aglycon and daunosamine as an aminosugar were detected by thin layer chromatography. Thus, the present substance is confirmed to be D788-7.

The object of the present invention, D788-7, is the compound expressed in formula (II) with antitumor activity.

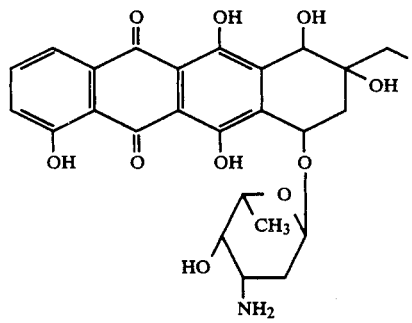
(II)

According to the process of the present invention, the industrial yield of D788-7 which has been extremely low can be increased to 30–70% (by weight).

DESCRIPTION OF THE PREFERRED EMBODIMENTS

The embodiments of the present invention are illustrated to describe the invention more specifically.

[EXAMPLES]

EXAMPLE 1.

Preparation of carborubicin

A scoop of the YS-slant culture [0.3% yeast extract, 1% soluble-starch, 1.5% agar, pH 7.2] of Streptomyces coeruleorubidus strain 3T-373 (FERM BP-165) is inoculated on the seed medium of 100 ml which is divided and sterilized in 500 ml Erlenmeyer flask and is incubated on rotary shaker at 200 rpm/min. at 28° C. for 3 days in order to prepare the seed.

| Seed medium | (w/v) |
|---|---|
| Soluble starch | 0.5% |
| Glucose | 0.5% |
| Essanmeat (soy bean powder, manufactured by Ajinomoto Co.) | 1.0% |
| Yeast extract | 0.1% |
| Sodium chloride | 0.1% |
| Potassium diphosphate | 0.1% |
| Magnesium sulfate (7H$_2$O) | 0.1% |
| Tap water | pH 7.4 (before sterilization) |

Then, the above seed medium of 750 ml (corresponds to 5%) was added for inoculation to the production medium (15 l) comprising the following compositions in a a sterilized jar-fermentator of 30 l.

| Production medium | (w/v) |
|---|---|
| Taiwan yeast | 5% |
| Soluble starch | 7.5% |
| Yeast extract | 0.3% |
| Sodium chloride | 0.2% |
| Calcium carbonate | 0.3% |
| Mixture of minerals* | 0.06% (v/v) |
| Tap water | pH 8.2 (before sterilization) |
| *CaSO$_4$.5H$_2$O | 2.8 g |
| FeSO$_4$.7H$_2$O | 0.4 g |
| MnCl$_2$.4H$_2$O | 3.2 g |
| ZnSO$_4$.7H$_2$O | 0.8 g |

The above substances are dissolved in 500 ml of water and a small amount of hydrogen chloride is added for preservation.

The cultivation was carried out at 28° C. for 140 hours (aeration; 5 l/min., agitation; 450 rpm/min.) to obtain the culture liquid in dark red-brown containing about 500 μg/ml of carborubicin (the amount of carborubicin; 7.25 g).

The culture liquid was recovered from the jar-fermentator and diluted to about 50 l (three times) with water and then phosphoric acid was added to adjust to pH 1.5 followed by agitation for about 1 hour. The filtering agent was added thereto at a ratio of 2% for filtration, and filtered to give the supernatant containing carborubicin (the extraction yield; 80%, carborubicin; 5.89 g).

This supernatant was passed through a column of the synthetic adsorption resin Diyaion HP-20 (1000 ml, pH 1.5) (manufactured by Mitsubishi Kasei Industries, Inc.) for adsorption and washed with diluted sulfuric acid (1000 ml, pH 1.5) and then with 20% acetone-water (1000 ml, pH 1.5), and eluted with 60% acetone-water (2000 ml, pH 1.5) to obtain acetone-eluted carborubicin of about 900 ml in acetone eluant (recovery yield by elution; 92%, 5.34 g).

EXAMPLE 2.

To 900 ml of acetone solution (acetone content; about 50%) of carborubicin, obtained in Example 1, was added acetone of 2100 ml and subsequently added 2M sodium citrate (30 ml) and iodine (5 g), followed by addition of 4N sodium hydroxide to adjust to pH 5.2. The resulting solution was taken into a tray made of stainless steel and high pressure Hg lamp (manufactured by Riko-Kagaku Industries, UVL-400H-300P type) was inserted thereinto for radiation while stirring for 1 hour (conversion rate; 48%, D788-7; 2.56 g).

To the reaction solution was added water (3000 ml) and chloroform (3000 ml) and extracted under agitation, while adjusting the aqueous phase to pH 8.0 using 4N sodium hydroxide. The organic phase was taken and washed with 20% sodium chloride (1 l) to concentrate at 45° C. under reduced pressure. An excess amount of hexane was added to the concentrate to precipitate the partially purified D788-7. The sediment was filtered and dried to yield the powder 2.79 g containing 2.3 g of pure D788-7.

The powder 2.74 g as obtained above was dissolved in the mixture of chloroform (50 ml) and methanol (2.5 ml) and while stirring, 2N hydrochloric acid-methanol (2.2 ml) is gradually dropped. The reaction mixture is stirred overnight to complete the crystallization followed by drying in vacuo and thus 1.88 g of the purified hydrogen chloride salt of D788-7 was obtained.

EXAMPLE 3.

To the carborubicin solution in acetone (about 1000 ml containing 6.56 g of carborubicin) was added acetone (2500 ml), 2M sodium citrate (35 ml) and iodine (6 g), and adjusted to pH 5.2 with 4N sodium hydroxide. The resulting solution was taken in a colorless glass bottle (volume; 5 l) for exposure to sun-light on a fine day for three hours under continuous stirring while adjusting pH to 5.0–5.5.

The conversion ratio into D788-7 was 58% and 3.8 g of D788-7 was produced.

To the reaction solution was added water (3000 ml) and chloroform (3000 ml) while the aqueous phase was adjusted to pH 8.0 for extraction under stirring. The organic phase was taken, washed by 20% sodium chloride and concentrated to a small amount at 45° C. under reduced pressure. An excess amount of hexane was added to precipitate the partially purified D788-7, which was filtered and dried to yield the powder 3.02 g containing 2.5 g of D788-7. This product was salified with hydrochloric acid in the same manner as in Example 2 to give 1.90 g of the purified hydrochloride of D788-7.

The hydrochloride of D788-7 shows the following physico-chemical properties;

Melting point: 182°–185° C. (degradation).

$[\alpha]^{23}$: +397° (c 0.02, in methanol).

UV and visible absorption spectra (in methanol).

$\lambda^{90\%}{}_{max}$methanol$_{nm}$($E^{1\%}{}_{1\ cm}$): 204 (326), 235 (754), 254 (433), 293 (144), 495 (274), 528 (178).

Infrared absorption spectrum $\nu^{KBr}{}_{max}$cm$^{-1}$: 3400, 3930, 1605, 1465, 1405, 1295, 1240, 1200, 1170, 1135, 1120, 1075, 1010, 990, 880, 830, 780.

| $^1$H-NMR spectrum (in CD$_3$OD) | |
|---|---|
| Proton | Chemical shift ($\delta$ ppm) |
| 1-H | 7.45 dd (J = 7, 4Hz) |
| 2-H | 7.43 t (J = 7 Hz) |
| 3-H | 7.00 dd (J = 7, 4Hz) |
| 7-H | 4.90 bs |
| 8-CH$_2$ | 2.0 ~ |
| 10-H | 4.73 s |
| 13-CH$_2$ | 1.7 ~ m |
| 14-CH$_3$ | 1.11 T (J = 7Hz) |
| 1'-H | 5.41 bs |
| 2'-CH$_2$ | 1.7 ~ m |
| 3'-H | 3.5 ~ m |
| 4'-H | 3.8 bs |
| 5'-H | 4.26 q (J = 7Hz) |
| 6'-CH$_3$ | 1.32 d (J = 7Hz) |

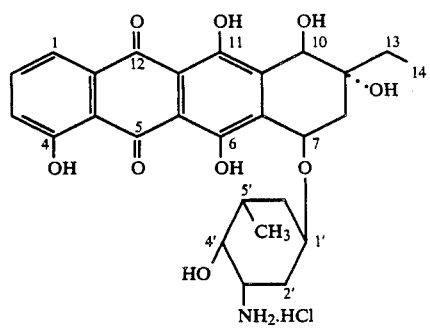

This invention is a process for preparing an antibiotic D788-7 possessing antitumor activity in a simple manner and in high yield. According to the invention, a large quantity of the substance in high quality useful as an antitumor agent can be produced. Thus, the present invention is defined as extremely useful.

What is claimed is:

1. A process for preparing an antibiotic D788-7 wherein carborubicin in acetone solution is exposed to light.

2. A process for preparing an antibiotic D788-7 wherein after culturing carborubicin-producing strain, the obtained culture liquid is extracted in acidic conditions while stirring to be adsorbed to synthetic resin, followed by desorption from the resin and elution with acetone and the resulting acetone solution containing carborubicin is converted into an antibiotic D788-7 by photo radiation, for obtaining D788-7 in the purified form from the reaction solution.

3. The process for preparing the antibiotic D788-7 according to claim 1 or 2 wherein the photo radiation is carried out by sunlight or an artificial light with main wavelength of about 3500 Å.

4. The process for preparing the antibiotic D788-7 according to claim 1 or 2 wherein the acetone solution containing carborubicin is a 50–100% acetone solution.

5. The process for preparing the antibiotic D788-7 according to claim 1 or 2 wherein iodine is added to the acetone solution containing carborubicin.

* * * * *